United States Patent

(12) United States Patent
Yamamoto et al.

(10) Patent No.: US 10,596,415 B2
(45) Date of Patent: Mar. 24, 2020

(54) RUNNING ANALYSIS DEVICE

(71) Applicant: CASIO COMPUTER CO., LTD., Shibuya-ku, Tokyo (JP)

(72) Inventors: Futoshi Yamamoto, Hamura (JP); Yuji Otani, Hachioji (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 235 days.

(21) Appl. No.: 15/719,488

(22) Filed: Sep. 28, 2017

(65) Prior Publication Data

US 2018/0147446 A1    May 31, 2018

(30) Foreign Application Priority Data

Nov. 29, 2016   (JP) .................... 2016-231159

(51) Int. Cl.
*A63B 24/00* (2006.01)
*A61B 5/11* (2006.01)
*G06K 9/00* (2006.01)
*G16H 20/30* (2018.01)
*G16H 40/63* (2018.01)
(Continued)

(52) U.S. Cl.
CPC .......... *A63B 24/0006* (2013.01); *A61B 5/112* (2013.01); *A63B 24/0062* (2013.01); *A63B 69/0028* (2013.01); *A63B 71/0622* (2013.01); *G06K 9/00348* (2013.01); *G06K 9/00536* (2013.01); *G16H 20/30* (2018.01); *G16H 40/63* (2018.01); *A61B 2562/0219* (2013.01); *A63B 2024/0009* (2013.01); *A63B 2071/0661* (2013.01); *A63B 2220/40* (2013.01); *A63B 2220/62* (2013.01); *A63B 2220/803* (2013.01);
(Continued)

(58) Field of Classification Search
CPC ............ A63B 24/0006; A63B 24/0062; A63B 2071/0661; A61B 5/112
See application file for complete search history.

(56) References Cited

U.S. PATENT DOCUMENTS 7,970,568 B1 * 6/2011 Schabowski ......... G01C 22/006
                                                              702/116
9,149,212 B2 * 10/2015 Mori .................... A61B 5/1038
(Continued)

FOREIGN PATENT DOCUMENTS

JP     2012179114 A    9/2012
JP     2014124448 A    7/2014
(Continued)

OTHER PUBLICATIONS

Japanese Office Action dated Oct. 16, 2018 (and English translation thereof) issued in counterpart Japanese Application No. 2016-231159.
(Continued)

*Primary Examiner* — Mohamed Charioui
(74) *Attorney, Agent, or Firm* — Holtz, Holtz & Volek PC

(57) ABSTRACT

A running analysis device includes a processor and a storage. In the storage, a program to be executed by the processor is stored. The processor performs an analysis process by which running of a user is analyzed using sensor data output from a sensor attached to the user. The analysis process includes an indicator identifying process of identifying, in a swing phase in a running cycle, a period that serves as an indicator.

9 Claims, 5 Drawing Sheets

(51) Int. Cl.
*A63B 69/00* (2006.01)
*A63B 71/06* (2006.01)

(52) U.S. Cl.
CPC ..... *A63B 2220/836* (2013.01); *A63B 2225/50* (2013.01)

(56) References Cited

U.S. PATENT DOCUMENTS

| | | | |
|---|---|---|---|
| 9,642,415 B2 | 5/2017 | Pease et al. | |
| 9,656,119 B2 | 5/2017 | Ura et al. | |
| 9,700,241 B2* | 7/2017 | Eastman | A61B 5/112 |
| 2010/0204615 A1* | 8/2010 | Kyle | A63B 24/0006 |
| | | | 600/595 |
| 2012/0253234 A1* | 10/2012 | Yang | A61B 5/1038 |
| | | | 600/595 |
| 2013/0178958 A1 | 7/2013 | Kulach et al. | |
| 2014/0188257 A1 | 7/2014 | Ura et al. | |
| 2015/0081245 A1 | 3/2015 | Nagasaka | |
| 2016/0029954 A1 | 2/2016 | Sato et al. | |
| 2016/0030804 A1 | 2/2016 | Mizuochi et al. | |
| 2016/0058373 A1 | 3/2016 | Anandabairavasamy | |
| 2017/0239551 A1 | 8/2017 | Pease et al. | |

FOREIGN PATENT DOCUMENTS

| | | |
|---|---|---|
| JP | 2016034482 A | 3/2016 |
| JP | 2016043260 A | 4/2016 |
| WO | 2012109244 A1 | 8/2012 |

OTHER PUBLICATIONS

Extended European Search Report dated Apr. 11, 2018 issued in counterpart European Application No. 17193464.9.
European Office Action dated Nov. 27, 2019 issued in counterpart European Application No. 17193464.9.

* cited by examiner

RUNNING ANALYSIS DEVICE

CROSS-REFERENCE TO RELATED APPLICATIONS

This application is based upon and claims the benefit of priority from the prior Japanese Patent Application No. 2016-231159, filed on Nov. 29, 2016, the entire contents of which are incorporated herein by reference.

BACKGROUND OF THE INVENTION

1. Field of the Invention

The present invention relates to a running analysis device.

2. Description of the Related Art

There has been disclosed a measurement device which can obtain, from output results of an acceleration sensor in the moving direction and the vertical direction when a person walks with the acceleration sensor attached, data relevant to a landing timing(s), a ground leaving timing(s) and a ground contact time(s) during the walk, for example. (Refer to, for example, Japanese Patent Application Publication No. 2012-179114.) The data relevant to the landing timing, the ground leaving timing and the ground contact time are utilized for running analysis, and it is considered, for example, that reducing the ground contact time can increase the running speed.

SUMMARY OF THE INVENTION

According to an aspect of the present invention, there is provided a running analysis device including: a processor; and a storage in which a program to be executed by the processor is stored, wherein the processor performs an analysis process by which running of a user is analyzed using sensor data output from a sensor attached to the user, and the analysis process includes an indicator identifying process of identifying, in a swing phase in a running cycle, a period that serves as an indicator.

BRIEF DESCRIPTION OF THE DRAWINGS

The present invention is fully understood from the detailed description given hereinafter and the accompanying drawings, which are given by way of illustration only and thus are not intended to limit the present invention, wherein.

DETAILED DESCRIPTION OF THE PREFERRED EMBODIMENTS

Hereinafter, one or more embodiments of the present invention are described in detail with reference to the drawings. However, the present invention is not limited to the illustrated examples.

Figure 1:
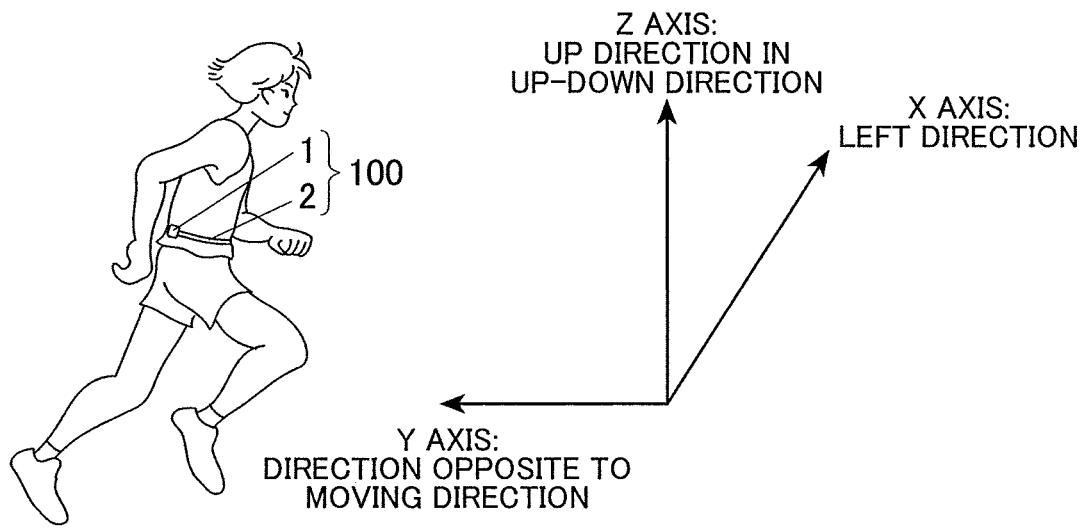
FIG. 1 is a diagram showing a state in which a running analysis device according to embodiment(s) of the present invention is attached to a user.

FIG. 1 is a diagram showing a state in which a running analysis device 100 according to an embodiment(s) of the present invention is attached to a user.

As shown in FIG. 1, the running analysis device 100 includes a main part 1 and a belt part 2. The main part 1 is fixed at the position of the waist of the user by the belt part 2. In this application, the right-left direction is X axis, the front-back direction is Y axis, and the up-down direction is Z axis. In X axis, the left direction is positive, and the right direction is negative. In Y axis, the direction opposite to the moving (running) direction is positive, and the moving direction is negative. In Z axis, the up direction is positive, and the down direction is negative.

The "running" in this application means running in a broad sense, and hence includes not only short-distance races, long-distance races and so forth at track and field events but also, what is called, jogging and so forth.

Figure 2:
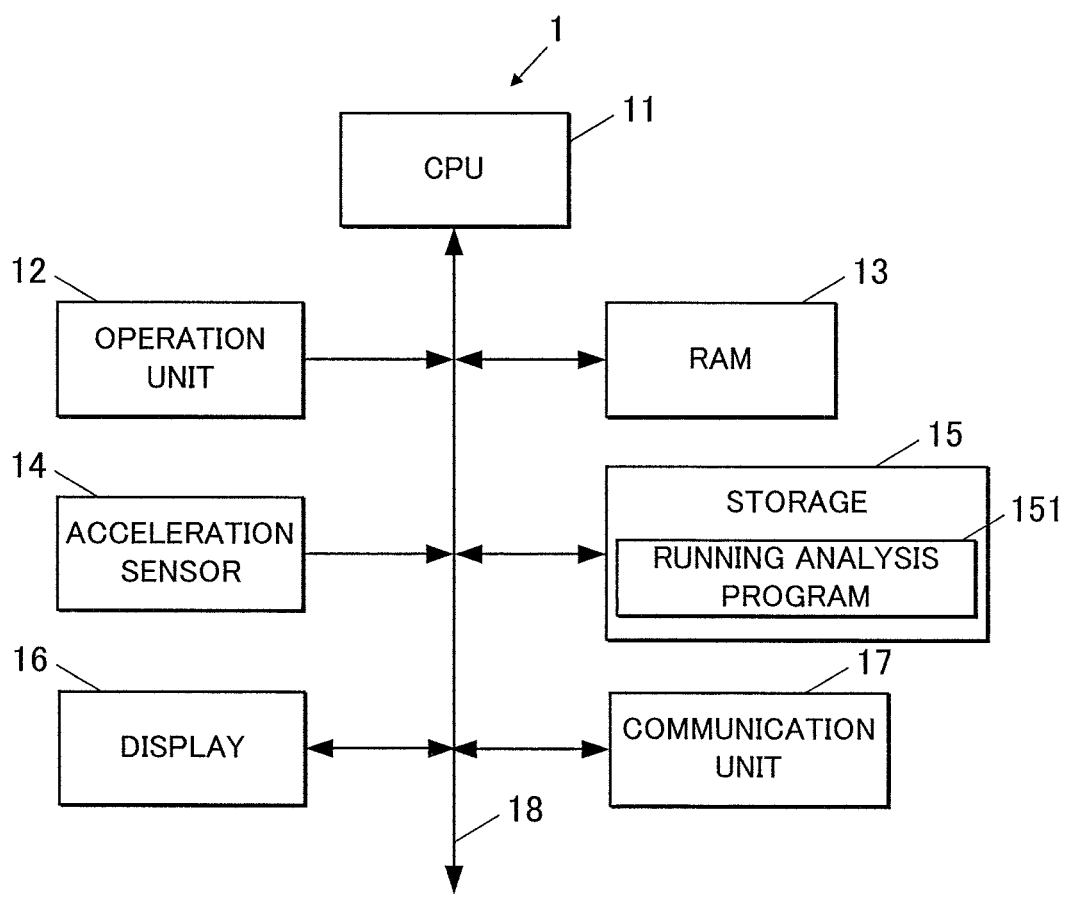
FIG. 2 is a block diagram showing the functional configuration of a main part of the running analysis device.

FIG. 2 is a block diagram showing main components of the main part (analyzer) 1 according to the embodiment, the main components for performing control.

As shown in FIG. 2, the main part 1 includes a CPU (Central Processing Unit) 11 as an indicator identifying unit, an operation unit 12, a RAM (Random Access Memory) 13, an acceleration sensor 14, a storage 15, a display 16 and a communication unit 17. These components of the main part 1 are connected to one another via a bus 18.

The CPU 11 controls the components of the main part 1. The CPU 11 reads programs specified from among a system program and application programs stored in the storage 15, opens the read programs on the RAM 13, and performs a variety of processes in cooperation with the opened programs. Further, the CPU 11 stores, in the storage 15, data of accelerations in the respective axes output from the acceleration sensor 14.

The operation unit 12 includes a power button (not shown) to turn on and off a power source, a start/stop button (not shown) to start and stop obtaining data, and a display switch button (not shown) to switch displayed contents. On the basis of commands from the operation unit 12, the CPU 11 controls the components of the main part 1.

The RAM 13 is a volatile memory and forms a work area where various data and programs are temporarily stored.

The acceleration sensor 14 detects accelerations in the respective directions of the three axes, which are at right angles to one another. The acceleration sensor 14 outputs data of the detected accelerations in the respective axes to the CPU 11.

The storage 15 is a storage which is constituted of a flash memory, an EEPROM (Electrically Erasable Programmable ROM) or the like and in and from which data and programs are writable and readable. The storage 15 stores therein a running analysis program 151 among others.

The display 16 is constituted of an LCD (Liquid Crystal Display), an EL (Electro Luminescence) display or the like, and performs a variety of display by following display information from the CPU 11.

The communication unit 17 outputs obtained data to an external information terminal(s) under the control of the CPU 11. The communication unit 17 is, for example, a wired communication unit such as a USB terminal or a communication unit using a near field wireless communication standard such as Bluetooth®.

Next, a running analysis process performed by the running analysis device 100 is described with reference to FIG. 3.

The running analysis process is described in a case where data of accelerations in the respective axes for a predetermined distance that a user has run is obtained in advance and stored in the storage 15. For example, when the start/stop button is operated to start obtaining data, a user starts and then finishes running a predetermined distance, and when the start/stop button is operated again to stop obtaining data, the CPU 11 performs the running analysis process in cooperation with the running analysis program 151, which the CPU 11 appropriately reads from the storage 15 and opens on the RAM 13.

Figure 3:
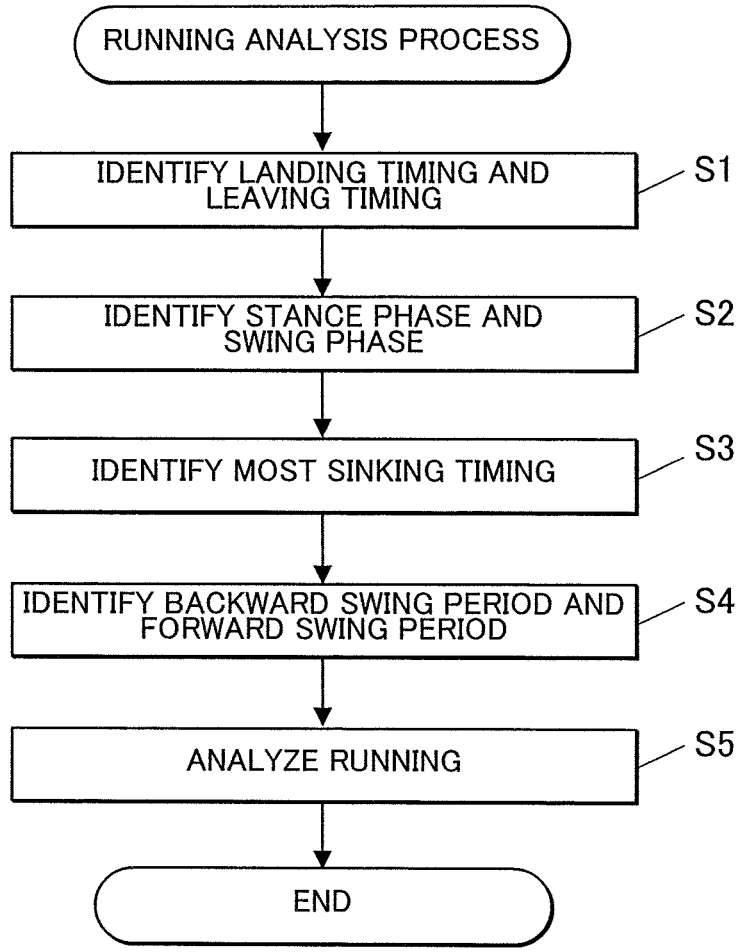
FIG. 3 is a flowchart of a running analysis process.

As shown in FIG. 3, when the CPU 11 starts the running analysis process, the CPU 11 identifies landing (ground contacting) timings and leaving (ground leaving) timings on the basis of the data of the accelerations in the respective axes (Step S1). The landing timings and the leaving timings can be identified by using a well-known art, and therefore detailed description thereof is omitted here.

Figure 4:
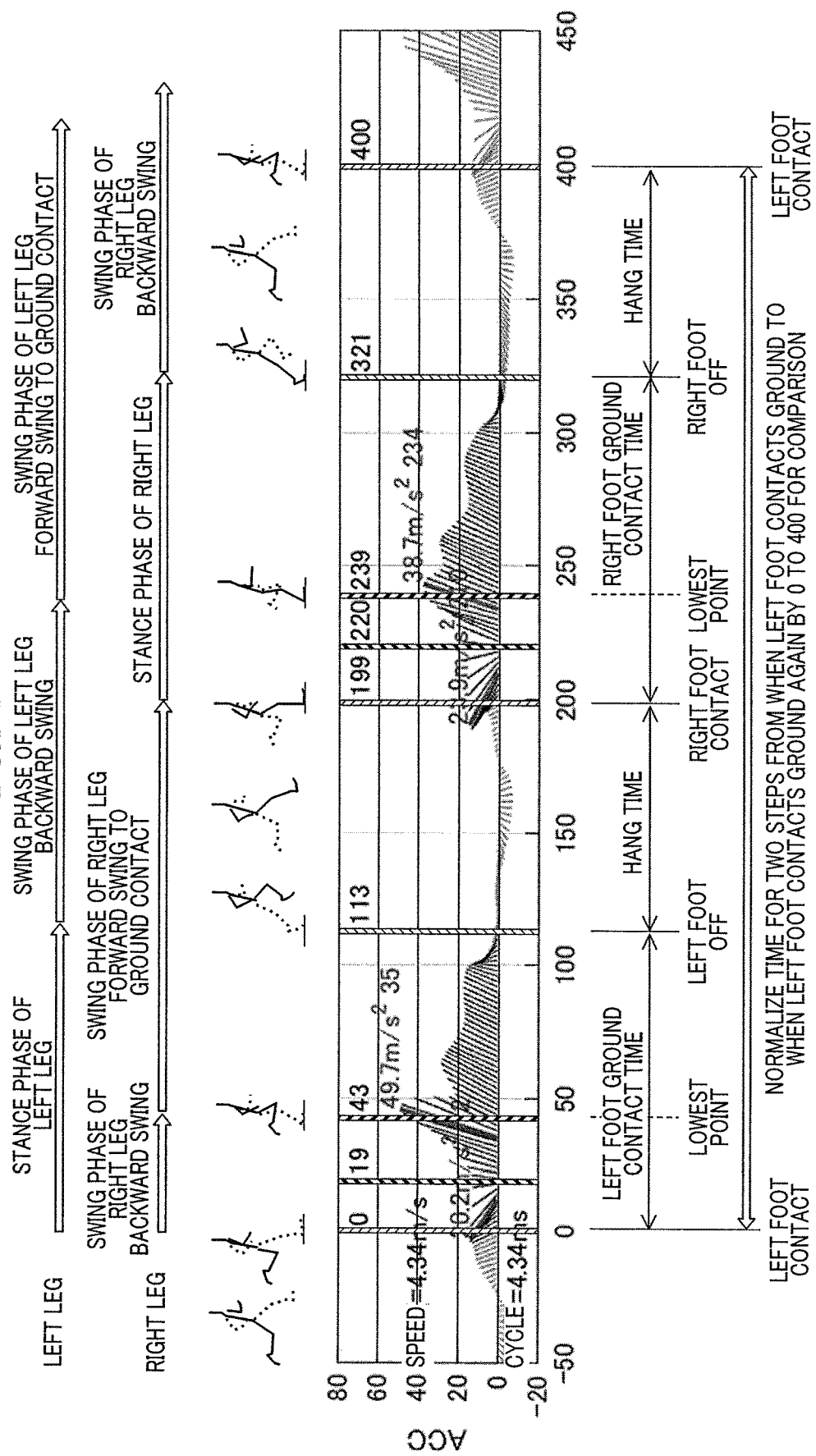
FIG. 4 shows a running cycle in a certain period of time.

Next, the CPU 11 identifies stance phases and swing phases of the right leg and the left leg on the basis of the landing timings and the leaving timings identified in Step S1 (Step S2). More specifically, as shown in FIG. 4, the CPU 11 identifies a period from "0" to "113" points, namely, a period from when the left foot contacts the ground to when the left foot leaves the ground as a stance phase (a stance phase of the left leg), and identifies a period from "113" to "400" points, namely, a period from when the left foot leaves the ground to when the left foot contacts the ground again, as a swing phase (a swing phase of the left leg). Similarly, the CPU 11 identifies a period from "199" to "321" points, namely, a period from when the right foot contacts the ground to when the right foot leaves the ground, as a stance phase (a stance phase of the right leg), and identifies a period from "0" to "199" points and from "321" to "400" points, namely, a period from when the right foot leaves the ground to when the right foot contacts the ground again, as a swing phase (a swing phase of the right leg). FIG. 4 shows data from when the left foot contacts the ground to when the left foot contacts the ground again in a certain period of time only, but in reality, in Step S2, the CPU 11 identifies stance phases and swing phases over the whole time that the user has run the predetermined distance. In FIG. 4, time for two steps from when the left foot contacts the ground to when the left foot contacts the ground again (running cycle) is expressed by normalized time (0 to 400 points).

Figure 5:
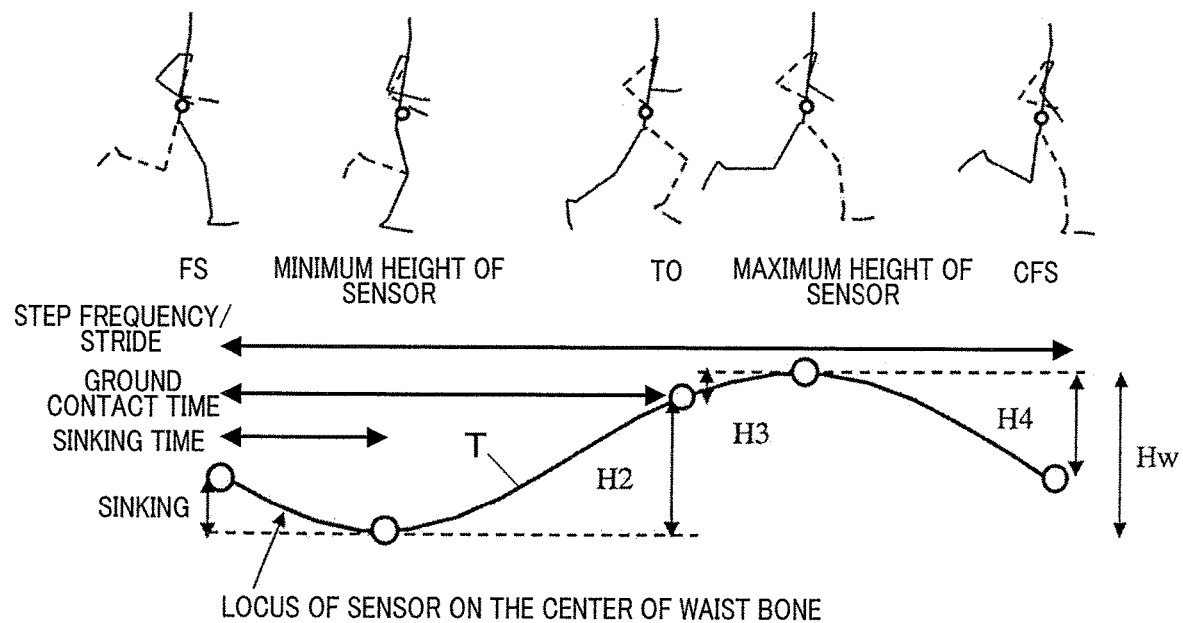
FIG. 5 shows most sinking timings (lowest points)

Next, the CPU 11 identifies, in the stance phase of each leg identified in Step S2, a timing at which the waist of the user, namely, the acceleration sensor 14, sinks most (Step S3). More specifically, the CPU 11 obtains a height position waveform T (shown in FIG. 5) showing the height position of the acceleration sensor 14 by integrating an acceleration signal(s) in Z axis twice, and then identifies a local minimum value of the height position waveform T in the stance phase of each leg as a most sinking timing (lowest point).

Next, by taking the most sinking timing (lowest point) of each leg identified in Step S3 as a reference, the CPU 11 identifies (separates) a forward swing period and (from) a backward swing period of the leg that is in the swing phase at the identified most sinking timing (Step S4). The backward swing period is a period in the swing phase, the period in which a leg of a user swings back (in the direction opposite to the moving direction of the user), whereas the forward swing period is a period in the swing phase, the period in which the leg of the user swings forward (in the moving direction of the user).

More specifically, as shown in FIG. 4, when "239" point is identified as the most sinking timing (lowest point), the CPU 11 identifies "113" to "239" points, namely, a period from when the left foot leaves the ground to when the most sinking timing is reached, as the backward swing period of the left leg, and identifies "239" to "400" points, namely, a period from when the most sinking timing is reached to when the left foot contacts the ground, as the forward swing period of the left leg.

As described above, it is desired to identify the backward swing period and the forward swing period by taking the most sinking timing (lowest point) as a reference. However, the method for identifying the backward swing period and the forward swing period is not limited thereto. For example, the CPU 11 may identify a maximum kick timing at which kicking power of kicking the ground in the stance phase of each leg identified in Step S2 is the maximum, and identify the backward swing period and the forward swing period by taking the maximum kick timing as a reference. Further, if the main part 1 is provided with a gyro sensor, the CPU 11 may identify an angle of rotation of the waist of the user on the basis of an angular velocity signal(s) output from the gyro sensor, identify a timing at which the angle of rotation of the waist is a predetermined value in the moving direction of the user, and identify the backward swing period and the forward swing period by taking the timing as a reference.

Here, the method for identifying the maximum kick timing is described with reference to the graph shown at the middle stage of FIG. 4. This graph is a graph in which the horizontal axis represents time, and, with time of each sampling point as the origin, the resultant vector of an acceleration vector in Z axis (vertical direction) and an acceleration vector in Y axis (horizontal direction) is drawn. That is, the graph shows change in the resultant vector over time, and the length of the line segment, which shows the resultant vector, indicates the magnitude of the acceleration.

First, the CPU 11 extracts sampling data of a section which is in the stance phase of each leg and in which values of acceleration data in Y axis are minus, namely, in which the user speeds up in the moving direction, and, for each extracted sampling data, adds up the square of the value of the acceleration data in Y axis and the square of the value of the acceleration data in Z axis and obtains the square root, thereby obtaining the magnitude of the acceleration on the YZ plane. Then, the CPU 11 identifies, in this section, time at which the magnitude of the acceleration is the largest (e.g. in FIG. 4, the timing of "35" point where 49.7 m/s$^2$ is displayed as the acceleration and the timing of "234" point where 38.7 m/s$^2$ is displayed as the acceleration) as the maximum kick timing.

Next, the CPU 11 analyzes the running of the user using data of the backward swing period and the forward swing period identified in Step S4 (Step S5) and ends the running analysis process.

Figure 6:
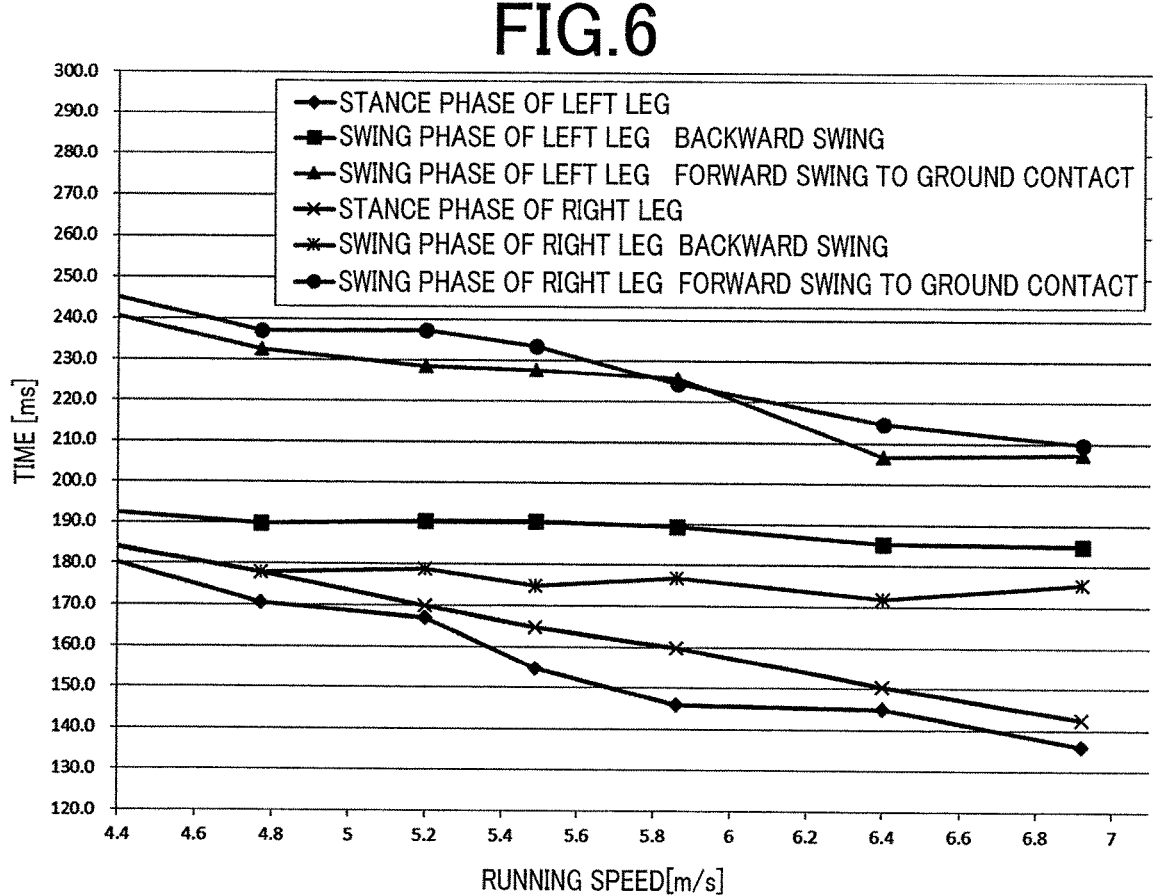
FIG. 6 shows an example of a running analysis result of a user.

FIG. 6 is a graph showing an example of a running analysis result of a user.

FIG. 6 shows time lengths spent on the stance phase, the backward swing period and the forward swing period of each leg in such a way as to be comparable by running speed. The time lengths spent on the stance phase, the backward swing period and the forward swing period of each leg are shown to check whether appropriate training has been done to make the backward swing period, which does not contribute to increase in the running speed, short while securing the sufficient forward swing period. If the forward swing period(s) is not long enough, the foot (feet) contacts the ground soon, and hence a hang time stride(s) does not lengthen, and also an action to return the leg(s) becomes insufficient, and hence heel contact tends to occur and accordingly braking at the time of contacting the ground becomes large. On the other hand, if the forward swing period(s) is relatively long (a forward swing rate is high), it directly contributes to stride lengthening, and also the action to return the leg becomes sufficient, and hence the foot can contact the ground near the center of gravity of the body and accordingly braking at the time of contacting the ground becomes relatively small, so that it brings increase in the running speed.

Figure 7A:
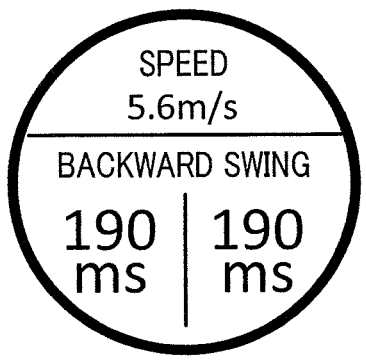
FIG. 7A is a display example showing the length of a backward swing period of each leg of a user when the user has run at a running speed of 5.6 m/s.
Figure 7B:
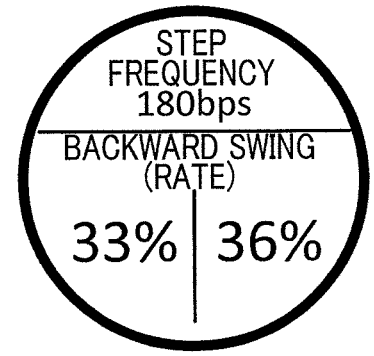
FIG. 7B is a display example showing a backward swing rate of each leg of the user when the user has run at a step frequency of 180 bps.
Figure 7C:
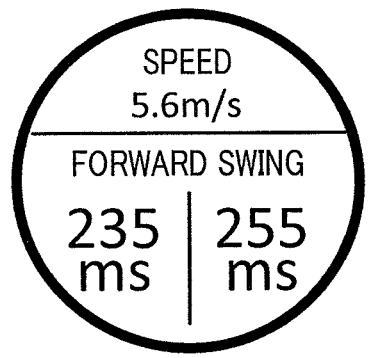
FIG. 7C is a display example showing the length of a forward swing period of each leg of the user when the user has run at a running speed of 5.6 m/s.
Figure 7D:
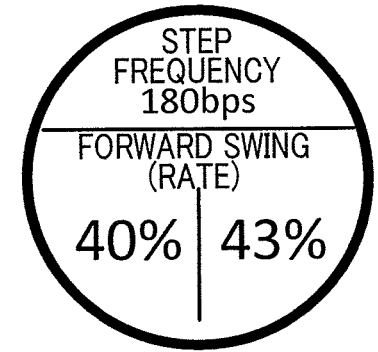
FIG. 7D is a display example showing a forward swing rate of each leg of the user when the user has run at a step frequency of 180 bps.

FIG. 7A to FIG. 7D show display examples in each of which data of a running analysis result is displayed on a display of an external information terminal (e.g. a running watch). More specifically, FIG. 7A is a display example showing the length of the backward swing period of each leg of a user when the user has run at a running speed of 5.6 m/s, and FIG. 7B is a display example showing a backward swing rate of each leg when the user has run at a step frequency of 180 bps. The backward swing rate is a value showing a ratio of the length of the backward swing period to that of the running cycle. FIG. 7C is a display example showing the length of the forward swing period of each leg when the user has run at a running speed of 5.6 m/s, and FIG. 7D is a display example showing a forward swing rate of each leg when the user has run at a step frequency of 180 bps. The forward swing rate is a value showing a ratio of the length of the forward swing period to that of the running cycle.

The data of the running analysis result is output to the external information terminal through the communication unit 17 of the main part 1.

Next, a result of training performed on the basis of an analysis result by the running analysis device 100 of the embodiment is described.

More specifically, a runner A ran with the running analysis device 100 attached, was given a training guidance based on the running analysis result to make the backward swing period short while securing the sufficient forward swing period, and actually went through the training by following the guidance.

As a result of that, although originally (before the training), at a step frequency of 190 bps, the average length of the backward swing periods was 222 ms, the average length of the forward swing periods was 262 ms, and the average stride was 190 cm, after the training, at the same step frequency (a step frequency of 190 bps), the average length of the backward swing periods was 215 ms, the average length of the forward swing periods was 271 ms, and the average stride was 193 cm.

That is, as compared with before the training, the backward swing period(s) decreased and the forward swing period(s) increased, and accordingly the stride(s) at the same step frequency lengthened.

As described above, according to the embodiment, the running analysis device 100 includes an analyzer (main part 1) that analyzes running of a user using sensor data output from the acceleration sensor 14 attached to the user, and the analyzer includes an indicator identifying unit (CPU 11) that identifies, in a swing phase in a running cycle, a period that serves as an indicator, and analyzes the running of the user on the basis of the period identified by the indicator identifying unit, the period serving as the indicator.

This makes it possible to evaluate the indicator, which is for increasing the running speed, and accordingly can efficiently increase the running speed.

Further, the running analysis device 100 identifies, as the period serving as the indicator, a backward swing period in which a leg of the user swings back and a forward swing period in which the leg of the user swings forward, the backward swing period and the forward swing period being included in the swing phase, and analyzes the running on the basis of the backward swing period and the forward swing period. This makes it possible to check whether appropriate training has been done to make the backward swing period, which does not contribute to increase in the running speed, short while securing the sufficient forward swing period, which contributes to increase in the running speed.

Further, the running analysis device 100 obtains a height position waveform showing a height position of the acceleration sensor 14 by integrating an acceleration signal(s) output from the acceleration sensor 14 twice, takes a timing at which the height position waveform shows a local minimum value as a most sinking timing of the user, and takes, of the swing phase, a period until the most sinking timing as the backward swing period and a period since the most sinking timing as the forward swing period. This makes it possible to identify the backward swing period and the forward swing period with high accuracy, and accordingly can accurately analyze running on the basis of the backward swing period and the forward swing period.

In the above, one or more embodiments of the present invention are described. Needless to say, however, the present invention is not limited thereto and can be appropriately modified in a variety of aspects without departing from the spirit of the present invention.

In the above embodiment(s), the graph in FIG. 6 is shown as a running analysis result of a user. The graph shows time lengths spent on the stance phase, the backward swing period and the forward swing period of each leg in such a way as to be comparable by running speed. However, the graph is a mere example and hence not a limit. It may be, for example, a graph showing time lengths spent on the stance phase, the backward swing period and the forward swing period of each leg in such a way as to be comparable by step frequency or a graph showing component rates of the running cycle (the stance phase, the backward swing period and the forward swing period) in such a way as to be comparable by running speed or step frequency.

Further, in the above embodiment(s), in order to derive a running analysis result of a user, the time length spent on the forward swing period of each leg is calculated. Alternatively or additionally, the distance that a user has moved in the forward swing period may be calculated. This is to keep a user from increasing the hang time wastefully by jumping upward (bouncing) in the forward swing period.

Further, in the above embodiment(s), data of a running analysis result is displayed on a display of an external information terminal (e.g. a running watch). However, how/where to display the data is not limited thereto. For example, data of a running analysis result may be displayed on the display 16 of the main part 1.

Further, in the above embodiment(s), data of accelerations in the respective axes for a predetermined distance that a user has run stored in the storage 15 in advance is analyzed. Additionally or alternatively, data of accelerations in the respective axes output from the acceleration sensor 14 while a user is running may be analyzed, and data of the analysis result may be displayed on the display 16 so that the user can check the analysis result while running.

Further, in the above embodiment(s), the running analysis device 100 is fixed at the position of the waist of the user, but may be fixed to (at the position of) a leg(s), the head or the like instead of the waist.

Further, in the above embodiment(s), as a computer readable medium for the programs of the present invention, a flash memory, an EEPROM or the like of the storage 15 is used. However, this is not a limit. As the computer readable medium, a portable recording/storage medium, such as a CD-ROM, can also be used. Further, as a medium to provide data of the programs of the present invention, a carrier wave can also be used.

In the above, one or more embodiments of the present invention are described. However, the scope of the present invention is not limited thereto and includes the scope of claims below and the scope of their equivalents.

What is claimed is:

1. A running analysis device comprising:
   a processor; and
   a storage in which a program to be executed by the processor is stored,
   wherein:
   the processor performs an analysis process by which running of a user is analyzed using sensor data output from a sensor attached to the user,
   the analysis process includes an indicator identifying process of identifying, in a swing phase in a running cycle, at least one of: (i) a backward swing period in which a leg of the user swings back, and (ii) a forward swing period in which the leg of the user swings forward, the backward swing period and the forward swing period being included in the swing phase, as a period that serves as an indicator;
   the sensor includes an acceleration sensor that outputs at least an acceleration signal in a front-back direction and an acceleration signal in a vertical direction as the sensor data, and
   the indicator identifying process is performed by: extracting the sensor data of a section in which the user speeds up in a moving direction; identifying a timing at which a sum of a square of a value of an acceleration in the front-back direction and a square of a value of an acceleration in the vertical direction is largest in the section as a maximum kick timing; and identifying, in the swing phase, a period until the maximum kick timing as the backward swing period and a period after the maximum kick timing as the forward swing period, thereby identifying at least one of the backward swing period and the forward swing period as the period that serves as the indicator.

2. The running analysis device according to claim 1, wherein:
   the indicator identifying process is performed by separating the period identified in the swing phase in the running cycle, the period serving as the indicator, and by the analysis process, the running of the user is analyzed based on the separated period serving as the indicator.

3. The running analysis device according to claim 1, wherein, by the analysis process, the running of the user is analyzed based on the period identified in the indicator identifying process, the period serving as the indicator.

4. The running analysis device according to claim 1, further comprising a display that displays an analysis result of the running of the user analyzed by the analysis process.

5. A running analysis method for a running analysis device, comprising:
   performing an analysis process by which running of a user is analyzed using sensor data output from a sensor attached to the user,
   wherein:
   the analysis process includes an indicator identifying process of identifying, in a swing phase in a running cycle, at least one of: (i) a backward swing period in which a leg of the user swings back, and (ii) a forward swing period in which the leg of the user swings forward, the backward swing period and the forward swing period being included in the swing phase, as a period that serves as an indicator,
   the sensor includes an acceleration sensor that outputs at least an acceleration signal in a front-back direction and an acceleration signal in a vertical direction as the sensor data, and
   the indicator identifying process is performed by: extracting the sensor data of a section in which the user speeds up in a moving direction; identifying a timing at which a sum of a square of a value of an acceleration in the front-back direction and a square of a value of an acceleration in the vertical direction is largest in the section as a maximum kick timing; and identifying, in the swing phase, a period until the maximum kick timing as the backward swing period and a period after the maximum kick timing as the forward swing period, thereby identifying at least one of the backward swing period and the forward swing period as the period that serves as the indicator.

6. The running analysis method according to claim 5, wherein:
   the indicator identifying process is performed by separating the period identified in the swing phase in the running cycle, the period serving as the indicator, and by the analysis process, the running of the user is analyzed based on the separated period serving as the indicator.

7. The running analysis method according to claim 5, wherein, by the analysis process, the running of the user is analyzed based on the period identified in the indicator identifying process, the period serving as the indicator.

8. The running analysis method according to claim 5, further comprising displaying, on a display, an analysis result of the running of the user analyzed by the analysis process.

9. A non-transitory computer readable storage medium storing a running analysis program that controls a computer to function as:
   an analyzer that analyzes running of a user using sensor data output from a sensor attached to the user,
   wherein:
   the analyzer includes an indicator identifying unit that identifies, in a swing phase in a running cycle, at least one of: (i) a backward swing period in which a leg of the user swings back, and (ii) a forward swing period in which the leg of the user swings forward, the backward swing period and the forward swing period being included in the swing phase, as a period that serves as an indicator,
   the sensor includes an acceleration sensor that outputs at least an acceleration signal in a front-back direction and an acceleration signal in a vertical direction as the sensor data, and the indicator identifying unit: extracts the sensor data of a section in which the user speeds up in a moving direction; identifies a timing at which a sum of a square of a value of an acceleration in the front-back direction and a square of a value of an acceleration in the vertical direction is largest in the section as a maximum kick timing; and identifies, in the swing phase, a period until the maximum kick timing as the backward swing period and a period after the maximum kick timing as the forward swing period, thereby identifying at least one of the backward swing period and the forward swing period as the period that serves as the indicator.

* * * * *